US010101494B2

(12) United States Patent
Badri et al.

(10) Patent No.: US 10,101,494 B2
(45) Date of Patent: Oct. 16, 2018

(54) MEASURING TOTAL ORGANIC CARBON OF SHALES USING THERMAL EXPANSION

(71) Applicant: Schlumberger Technology Corporation, Sugar Land, TX (US)

(72) Inventors: Mohammed Badri, Al-Khobar (SA); Reza Taherian, Missouri City, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 180 days.

(21) Appl. No.: 15/159,425

(22) Filed: May 19, 2016

(65) Prior Publication Data

US 2017/0336528 A1 Nov. 23, 2017

(51) Int. Cl.

| | |
|---|---|
| ***G01V 9/00*** | (2006.01) |
| ***E21B 33/12*** | (2006.01) |
| ***E21B 49/00*** | (2006.01) |
| ***E21B 49/06*** | (2006.01) |
| *G01N 25/16* | (2006.01) |
| *E21B 25/00* | (2006.01) |

(52) U.S. Cl.

CPC .............. *G01V 9/005* (2013.01); *E21B 33/12* (2013.01); *E21B 49/00* (2013.01); *E21B 49/06* (2013.01); *E21B 25/00* (2013.01); *G01N 25/16* (2013.01)

(58) Field of Classification Search

CPC ...................................................... G01V 9/005
USPC ...................................................... 73/152.54
See application file for complete search history.

(56) References Cited

U.S. PATENT DOCUMENTS 4,646,565 A * 3/1987 Siegfried ................. G01V 1/46 181/105
5,912,459 A 6/1999 Mullins et al.
2005/0206890 A1* 9/2005 Hurst ..................... G01N 33/24 356/239.7
2008/0198375 A1 8/2008 DiFoggio
(Continued)

FOREIGN PATENT DOCUMENTS

WO WO2013191886 A1 12/2013

OTHER PUBLICATIONS

Interntional Search Report (3 pages) regarding PCT/us17/031175, dated Aug. 18, 2017.*

(Continued)

*Primary Examiner* — Manish S Shah
*Assistant Examiner* — Jean Morello

(57) ABSTRACT

A tool having an energy source and a surface roughness measurement device is provided. A baseline measurement of surface roughness of a sample is made. The sample is then exposed to energy from the energy source, causing the temperature of the sample to increase. A second measurement of surface roughness of the sample is made. The change in surface roughness of the sample is determined. Formation properties such as the total organic carbon in the sample is inferred based on the determined change in surface roughness of the sample. The tool may be disposed in a wellbore and may use packers to isolate a portion of the wellbore, or it may use a hydraulic seal on an extendible member to isolate a sample portion of the wellbore wall. The energy source may be a laser that produces radiation that selectively heats a particular component of the sample constituent material.

23 Claims, 7 Drawing Sheets

510
510
520
530
560
540
550
530

(56) References Cited

U.S. PATENT DOCUMENTS

| | | | | |
|---|---|---|---|---|
| 2015/0088427 | A1* | 3/2015 | Rahmes | G01V 9/005<br>702/11 |
| 2016/0069177 | A1* | 3/2016 | Badri | G01J 5/00<br>250/269.1 |
| 2016/0349174 | A1* | 12/2016 | Washburn | G01N 21/272 |

OTHER PUBLICATIONS

Written Opinion of the International Search Authority (12 pages) regarding PCT/us17/031175, dated Aug. 18, 2017.*

* cited by examiner

MEASURING TOTAL ORGANIC CARBON OF SHALES USING THERMAL EXPANSION

BACKGROUND

Total organic carbon (TOC) is a commonly sought property of a hydrocarbon-bearing subsurface formation. In recent years the level of interest in the measurement of this property has increased even further with the emergence of shale oil and shale gas exploration and production. The shale formations being explored are typically more complex than conventional reservoir formations and they pose many more challenges in their petrophysical studies and interpretations. Many of the standard measurement techniques commonly used in conventional formations, such as measuring the TOC, do not work in shale. Traditionally TOC is derived from sonic or density logs. Both of those methods involve either prior knowledge or an accurate estimate of the matrix properties before the data can be interpreted. Estimation of matrix properties is not trivial for shale formations due to the high variability of constituent minerals and the possible presence of trace minerals such as pyrite, for example.

Shale formations are highly laminated and their depositional histories and transformation processes generally vary. The lamination thickness is not constant, but rather may vary anywhere in the range of millimeters to meters. As a result, high resolution measurements with short spacing between the sampling points can be important for evaluating the shales and to ensure any decision on the quality and economic potential of the formation reflects the real system.

Laser induced pyrolysis (LIP) has been used to make certain formation evaluation measurements uphole, at the surface. For example, LIP has been applied to core samples. LIP may also be used on rock cuttings flushed to the surface while drilling. However, one generally has no idea of the depth within the well from which the cutting came. That is, during drilling operations pieces of rock are cut and brought to the surface by the circulating drilling fluid (mud). While the mud travels to the surface, it experiences turbulent flow, causing the cuttings to mix and their relative depth information to be lost. In relatively homogeneous formations, measurements at the surface may succeed. However, shale cuttings, with their associated variable laminations, should not be considered to be from a homogeneous formation. A LIP measurement on a cutting may provide a high resolution map of the lamination of that cutting, albeit with uncertain depth information, but the obtained lamination map is generally not representative of the lamination of the shale reservoir.

The organic shales (oil or gas shale) are made of an inorganic matrix within which organic patches may be distributed. The organic patches may contain kerogen, for example, which is a source of producible oil or shale, and the kerogen content and its maturity are primary measures of producible liquid and gas hydrocarbons in these formations. Thus, its measurement provides an important parameter to assess the economic value of a particular shale formation. The percentage of kerogen is reported as total organic carbon (TOC). Higher TOC in a formation is expected to correlate with a higher volume of generated hydrocarbons (assuming the same maturity). Kerogen in the pore space also acts as a reservoir by adsorbing gas molecules inside the nano-pores that are present in its structure (i.e., intra-kerogen). Thus, quantifying TOC is an initial process in evaluating any shale gas or shale oil reservoir.

SUMMARY

A tool having an energy source and a surface roughness measurement device is provided. A baseline measurement of surface roughness of a sample is made. The sample is then exposed to energy from the energy source, causing the temperature of the sample to increase. A second measurement of surface roughness of the sample is made. The change in surface roughness of the sample is determined. Formation properties such as the total organic carbon in the sample is inferred based on the determined change in surface roughness of the sample. The tool may be disposed in a wellbore and may use packers to isolate a portion of the wellbore, or it may use a hydraulic seal on an extendible member to isolate a sample portion of the wellbore wall. The energy source may be a laser that produces radiation that selectively heats a particular component of the sample constituent material.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. Embodiments are described with reference to the following figures. The same numbers are generally used throughout the figures to reference like features and components.

DETAILED DESCRIPTION

Figure 1A:
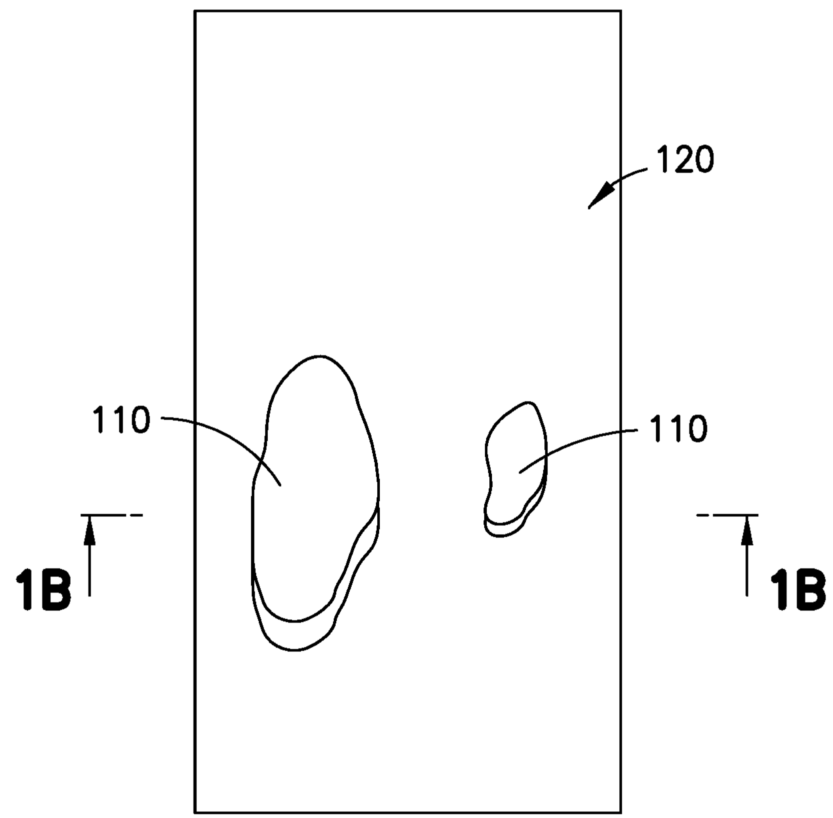
FIG. 1A is a perspective view of a sample of shale that contains organic patches within inorganic minerals, in accordance with the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Some embodiments will now be described with reference to the figures. Like elements in the various figures may be referenced with like numbers for consistency. In the following description, numerous details are set forth to provide an understanding of various embodiments and/or features. However, it will be understood by those skilled in the art that some embodiments may be practiced without many of these details and that numerous variations or modifications from the described embodiments are possible. As used here, the terms “above” and “below”, “up” and “down”, “upper” and “lower”, “upwardly” and “downwardly”, and other like terms indicating relative positions above or below a given point or element are used in this description to more clearly describe certain embodiments. However, when applied to equipment and methods for use in wells that are deviated or horizontal, such terms may refer to a left to right, right to left, or diagonal relationship, as appropriate. It will also be understood that, although the terms first, second, etc. may be used herein to describe various elements, these elements should not be limited by these terms. These terms are only used to distinguish one element from another.

The terminology used in the description herein is for the purpose of describing particular embodiments only and is not intended to be limiting. As used in the description and the appended claims, the singular forms “a”, “an” and “the” are intended to include the plural forms as well, unless the context clearly indicates otherwise. It will also be understood that the term “and/or” as used herein refers to and encompasses any and all possible combinations of one or more of the associated listed items. It will be further understood that the terms “includes,” “including,” “comprises,” and/or “comprising,” when used in this specification, specify the presence of stated features, integers, steps, operations, elements, and/or components, but do not preclude the presence or addition of one or more other features, integers, steps, operations, elements, components, and/or groups thereof.

As used herein, the term “if” may be construed to mean “when” or “upon” or “in response to determining” or “in response to detecting,” depending on the context. Similarly, the phrase “if it is determined” or “if [a stated condition or event] is detected” may be construed to mean “upon determining” or “in response to determining” or “upon detecting [the stated condition or event]” or “in response to detecting [the stated condition or event],” depending on the context.

A system and method to measure the hydrocarbon content or total organic carbon (TOC) of a rock formation by determining the difference in the thermal expansion of a shale rock solid (matrix) and the organic material (e.g., kerogen) contained within the matrix pore space is disclosed. A heat source such as a laser or an oven is used to heat a rock sample, causing the temperature of the sample to increase. The temperature increase leads to higher expansion of kerogen compared to the rock solid, thereby increasing the surface roughness of the sample. For ease of discussion, the term “kerogen” is used herein as a representative example of an “organic patch”, and, unless the context dictates otherwise, is not meant to be limited to kerogen. The surface roughness is then measured using, for example, mechanical or optical means. The excess (i.e., increase in) surface roughness is related to the percentage of kerogen on the surface, which in turn is considered to be a measure of TOC. This permits an estimation of TOC that is independent of or insensitive to the inorganic mineralogy.

Thermal heating of materials using a laser is well known. Use of a mechanical stylus to map the roughness of the surface is an established method in surface metrology. Also, use of optical interferometry to quantify the surface roughness is known in the art. Thus, the specifics of these techniques are not described in detail herein, though they, among other, are techniques that may be used to measure surface roughness in accordance with this disclosure.

The underlying physical characteristic exploited by the techniques disclosed herein relies on the contrast between the low thermal expansion of the background minerals and the higher thermal expansion of organic carbon to measure TOC. The change in the length of a sample as a result of a change in the temperature is given by:

$$\Delta L = L_0 \alpha (T_1 - T_0) \quad (1)$$

where $L_0$ is the initial length of the sample (at temperature $T_0$), $\Delta L$ is the change in length resulting from the temperature being changed to $T_1$, and $\alpha$ is the linear thermal expansion coefficient (LTEC) of the material under study.

Figure 1B:
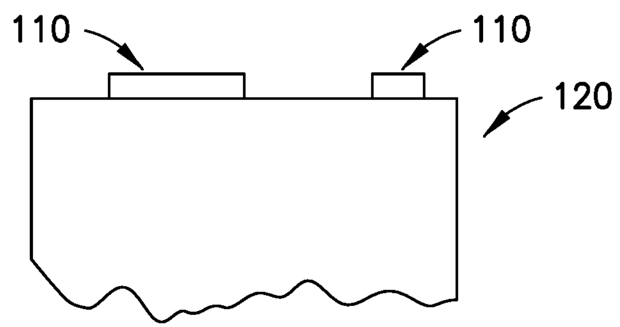
FIG. 1B is a cross-sectional view of the sample of FIG. 1A showing the organic patches and inorganic minerals at approximately the same level, in accordance with the present disclosure.

In one embodiment the sample surface is heated uniformly, for example by placing the sample in an oven. For composite materials in which more than one material is present on the surface, each component expands proportionally to its own LTEC. FIG. 1A is a perspective view of a sample of shale that contains patches of kerogen 110 along with inorganic minerals 120. FIG. 1B is a cross-sectional view of the sample of FIG. 1A showing the kerogen patches 110 and inorganic minerals 120 at approximately the same level, i.e. they form a relatively smooth surface. For purposes herein, the surface should be reasonably smooth.

Figure 1C:
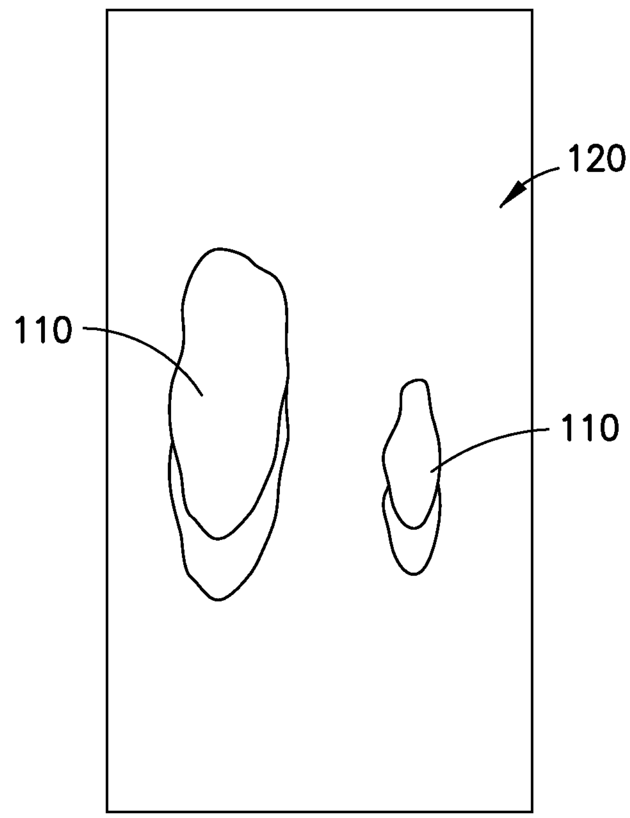
FIG. 1C is a perspective view of the sample of FIG. 1A showing the organic patches thermally expanded relative to the inorganic minerals, in accordance with the present disclosure.
Figure 1D:
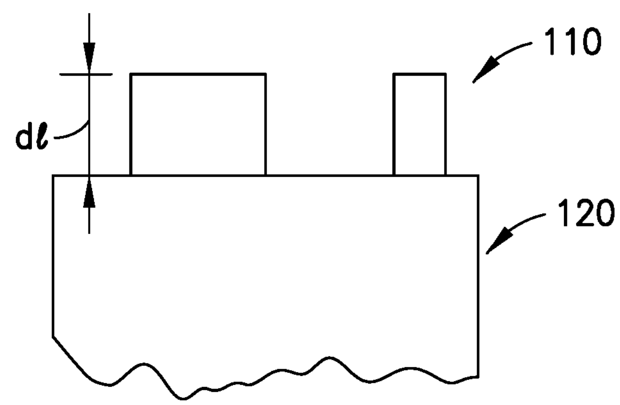
FIG. 1D is a cross-sectional view of the sample of FIG. 1A showing the organic patches and inorganic minerals at different levels due to unequal thermal expansion, in accordance with the present disclosure.

As the temperature of the sample increases, both components 110, 120 expand, each proportionally to its own LTEC. (The terms “component” or “components” as used above refer generically to either kerogen or the background minerals singularly or collectively.) The LTEC for the inorganic minerals 120 varies between (1 to 15)($10^{-6}$) meter/(meter K) while that of kerogen 110 is expected to be similar to large organic molecules such as organic polymers that have a LTEC of 100 meter/meter K or more. As a result, the fraction of shale surface filled by kerogen will expand about ten times more than the background minerals. This is shown in FIGS. 1C and 1D, which correspond to FIGS. 1A and 1B, respectively, but with the components in their expanded state after the temperature increase. The kerogen patches 110 have notably higher heights (dl) compared to the background mineral surface 120. Note that both the kerogen 110 and the inorganic minerals 120 expand and dl represents the net difference between how much the kerogen 110 expanded versus how much the background minerals 120 expanded. Using Equation (1), the net difference dl is given by:

$$dl = \Delta L_1 - \Delta L_2 = (\alpha_1 - \alpha_2)(T_1 - T_0) \quad (2)$$

where $\Delta L_1$ is the thermal expansion due to kerogen 110 and $\Delta L_2$ is the thermal expansion due to background minerals 120. For simplicity, equation (2) assumes that $L_0$ is the same for both materials and is assumed to be a unit length; i.e., there is a similar depth of penetration of the heat in the sample. Also, for FIGS. 1A-1D, it is assumed the various constituent minerals comprising the background minerals 120 have roughly the same LTEC, and all combine to form what is referred to as the background minerals.

As FIGS. 1A-1D demonstrate, the effect of increasing temperature is to increase the surface roughness by a factor proportional to the difference between the LTEC of the two materials. Thus, measuring surface roughness leads to a value for dl that can be integrated across a section of the surface studied to estimate the surface density of kerogen compared to the background minerals. The surface roughness can therefore be quantified and used to estimate the areas of the kerogen patches, which are taken to be proportional to TOC.

Figure 2:
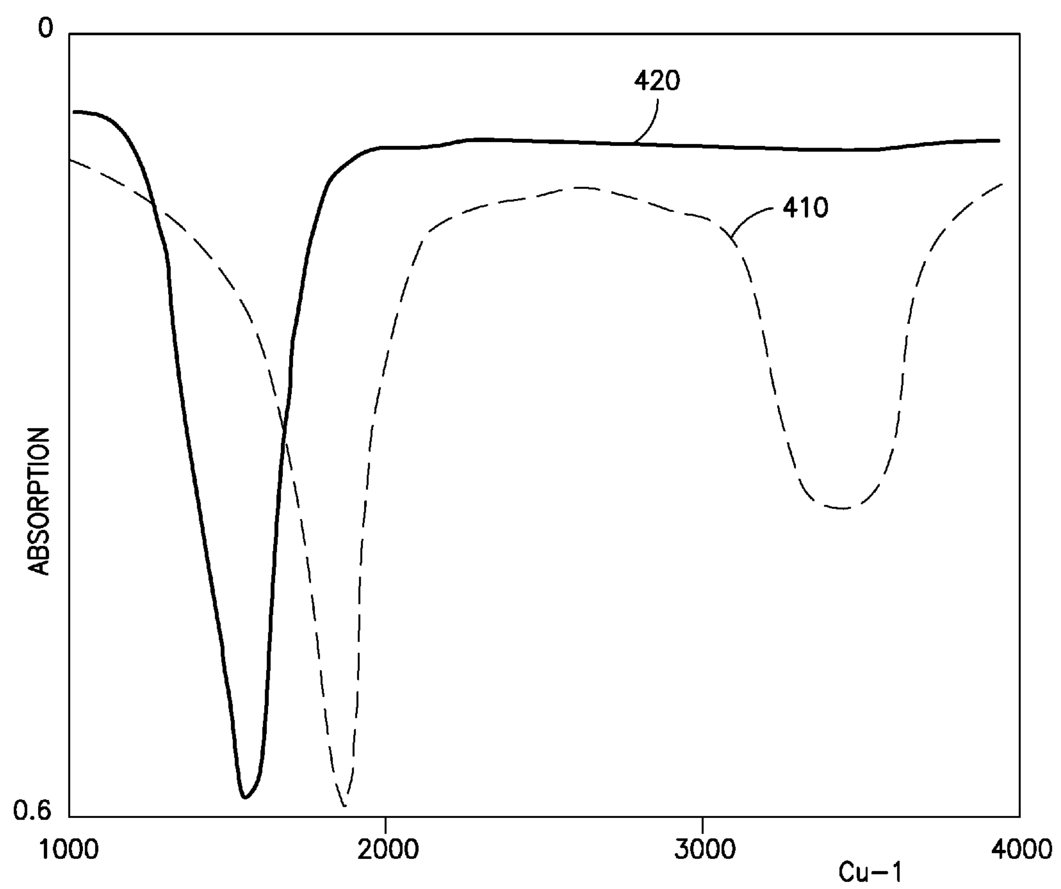
FIG. 2 is a plot of energy absorption versus wavelength of irradiated energy for two constituent components of a sample, in accordance with the present disclosure.

In another embodiment the surface is not heated uniformly. Rather, either the kerogen or the background minerals are selectively heated. As before, this causes the surface roughness to increase, which can be quantified to determine the TOC. In the heating method of this embodiment, the difference in the absorption spectrum of kerogen and the background minerals is used to selectively heat one or the other. For example, an infrared (IR) laser may be used to illuminate and selectively heat the surface. The radiation from the laser is selectively absorbed by the surface components based on their absorption spectra. In FIG. 2 the IR absorption spectra of kerogen and clay minerals are plotted together for comparison. Kerogen spectrum 410 is characterized by two broad peaks centered at 1600 $cm^{-1}$ and 3600 $cm^{-1}$. (The $cm^{-1}$, or wavenumber, is a common unit in the art of IR spectroscopy.) Note the low absorption in the range between those two peaks. The spectrum of clay minerals 420 shows a broad absorption centered at 1400 $cm^{-1}$. Thus, if a laser source close to or slightly less than 1400 $cm^{-1}$ is used to excite the surface, the minerals predominantly absorb the radiation and get heated. Due to the low absorption of the laser energy by kerogen at this wavelength range, the kerogen absorbs only a small fraction of the radiation. The heat causes the minerals to expand per Equation (1). In this scenario the minerals are enlarging at the expense of kerogen. However, because of the large difference in LTEC, the minerals may absorb more than ten times as much energy as the kerogen to produce a significant effect.

On the other hand, if a laser with radiation at or near 3600 $cm^{-1}$ is used to excite the surface, kerogen predominately absorbs the IR energy and its temperature increases. Again Equation (1) determines the length (in the one dimension considered) of each kerogen patch increase, causing the surface to become rougher. In this case, the surface roughness results from kerogen patches extending above the background mineral surface. Tuneable lasers covering this energy (i.e., frequency) range are commercially available. In either case (i.e., uniform or selective heating), techniques of quantifying the surface roughness may be used to measure the changes in surface roughness due to the heating.

In at least one embodiment, all the available techniques for measuring surface roughness are available and can be used to measure the surface roughness of the shale sample. This applies, for example, to cases for which the shale sample is available uphole. Examples include (but are not limited to) coring and mud gas logging in which cuttings are brought to the surface and are available for measurement. For such a case, the cutting(s) or core sample(s) is reasonably polished before applying the standard techniques used to map surface roughness. One such standard technique uses a stylus, which is a mechanical device. A stylus comprises a mechanical rod with a fine tip and is useful for cases where the kerogen patches are relatively large (e.g., on the order of microns). Many commercial instruments with resolution as low as two micrometers are available. To make a measurement the stylus is brought into contact with the surface from an established point and the distance traveled is measured. The surface roughness can also be measured optically using, for example, optical interferometry. Optical interferometry is a very common method for high precision examination of surface topography. Different methods of performing interferometry have been developed. One example is vertical scanning interferometry (VSI), which uses white light. It is a useful technique for mapping surfaces having a roughness range from centimeter to micrometer.

Figure 3:
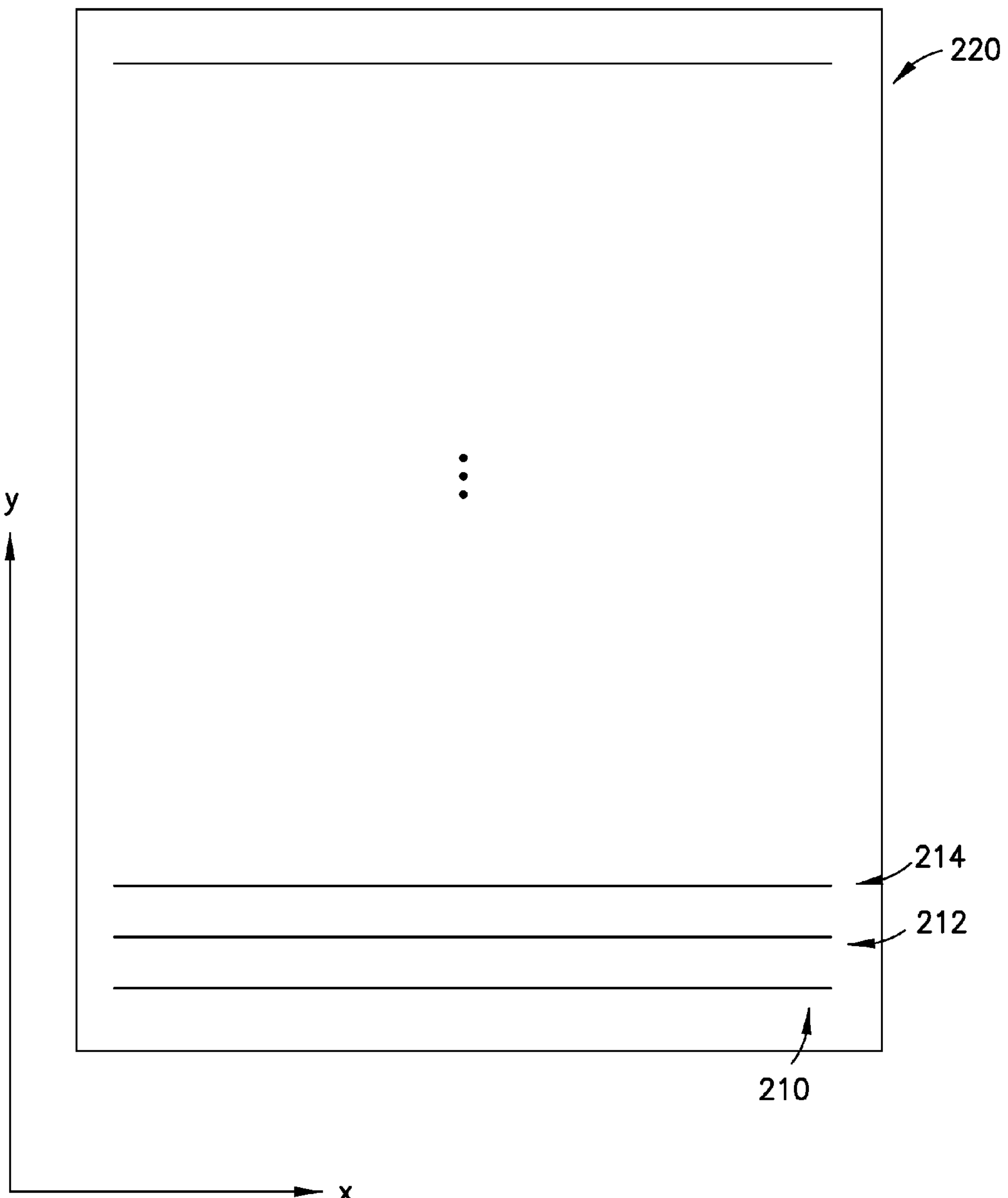
FIG. 3 is a schematic drawing of a plot of the various surface profiles produced from individual scans, in accordance with the present disclosure.

As FIG. 3 shows, the surface (x-y plane) may be scanned along one direction (say, the x-direction) while not moving in the other (i.e., y-) direction to generate a first profile 210. Then an incremental step is made in the fixed (i.e., y-) direction and the scan along the x-direction is repeated to generate a second profile 212, a third profile 214, etc. This is continued until the region of interest is covered, the last profile being indicated in FIG. 3 by profile 220. The map thereby obtained is a 2-D map of the surface roughness (i.e., the relative heights of components) and the areas corresponding to substantially equal height components can be integrated to provide an estimate of the relative area of the higher surface component compared to the total surface area.

In operation, the surface is initially mapped (e.g., by performing multiple scans) before increasing the temperature to provide an estimate of the initial or background roughness (i.e., the sample in the state shown in FIGS. 1A and 1B). The surface is then heated using an oven, a laser, or some other suitable energy source, causing the sample surface roughness to change (i.e., corresponding to the state shown in FIGS. 1C and 1D). Scans are then performed some desired number of times until the sample is adequately covered. The second (higher temperature) image is expected to have higher surface roughness. Comparing the two measurements provides an estimate of the fraction (or percentage) of the total surface that has protruded as a result of the temperature change. Such surface roughness may be attributed, for example, to the kerogen patches, from which the percentage of kerogen may be calculated.

Figure 4:
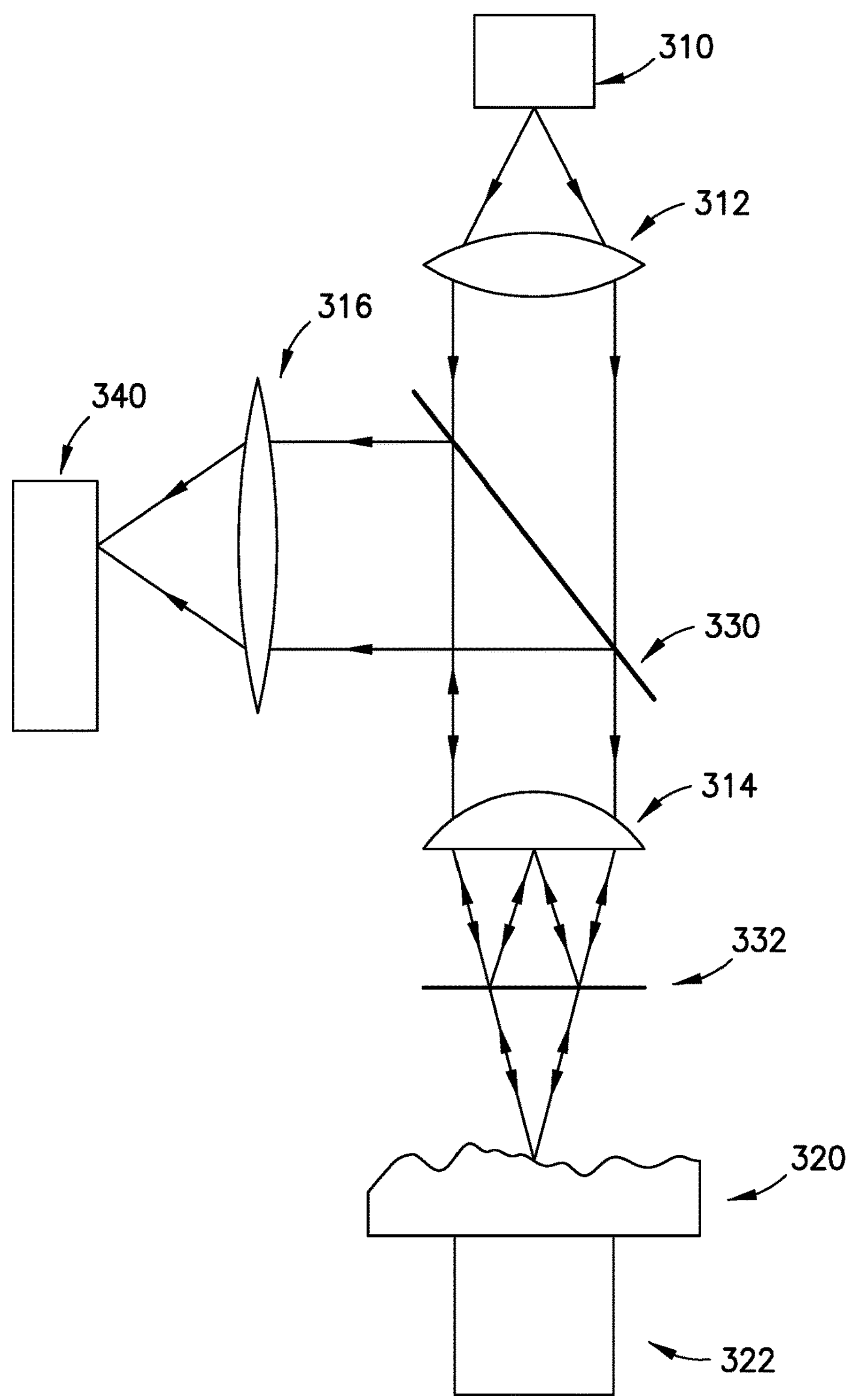
FIG. 4 is a schematic drawing of one embodiment of an optical interferometer surface roughness measurement device, in accordance with the present disclosure.

FIG. 4 shows a further embodiment. Optical interferometry is well know so this particular embodiment is described at a high level. A light source 310 provides white light that is shaped into a parallel beam by the lens 312. The light is refocused by lens 314 on the rough surface of the sample 320. However, a portion of this radiation is removed by the beam splitter 332 and is sent to the detector 340. The light reflected from the surface of the sample 320 travels back towards and is re-directed to the detector 340 so that two different light beams arrive at detector 340. The two beams pass back through the lens 314 and are reflected towards the detector 340 and lens 316 by the beam splitter 330. At the detector 340 the two light beams form an interference pattern from which the height of the sample surface 320 at the focal point can be determined. The sample is scanned (i.e., the focal point is varied) by either moving the interferometer or the sample 320 using the piezoelectric crystal 322. As described above, the region of interest is sampled before and after heating the sample and the difference in surface roughness may be attributed to the kerogen. The areal percentage of kerogen is assumed to be representative of the volumetric percentage.

In another embodiment an atomic force microscope (AFM) is used to map the surface roughness (topography) of the sample. AFM is readily available commercially. AFM is capable of mapping the surface roughness down to sub-micrometer scales. Other scanning microscopy techniques and apparatuses may also be used.

In another embodiment a measurement tool is used in situ under downhole conditions. For example, after a well is drilled and zones of interest are selected, a wireline or logging-while-drilling (LWD) tool may be sent to the depth(s) of interest and the TOC measured using the thermal expansion difference of the shale oil or shale gas component relative to the matrix material.

Figure 5:
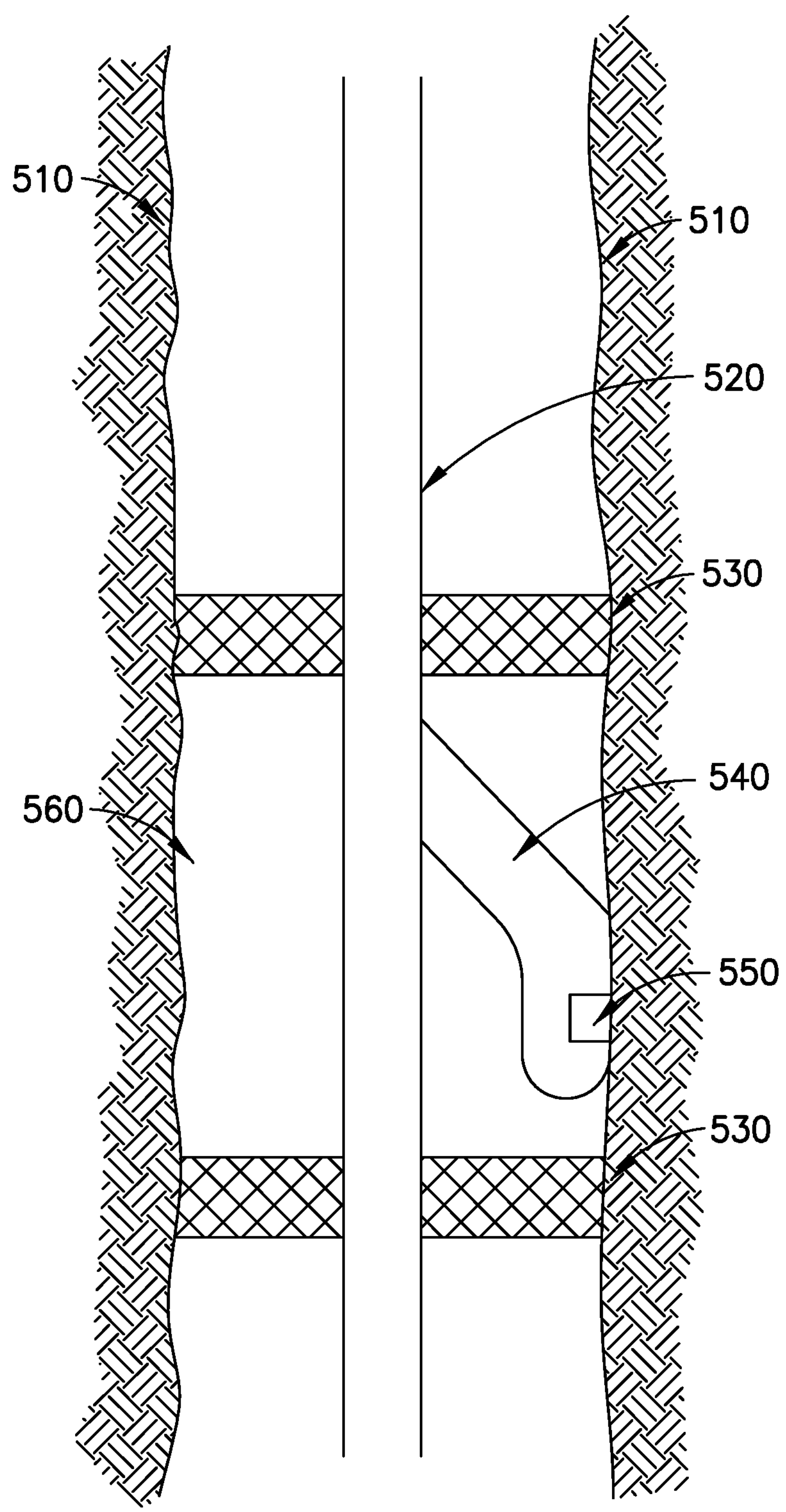
FIG. 5 is a schematic drawing of one embodiment of a downhole logging tool that can be part of a logging-while-drilling (LWD) or wireline suite of tools, in accordance with the present disclosure.

FIG. 5 shows an example design for a downhole logging tool 520 that can be part of an LWD or wireline suite of tools. A section 560 of the well 510 is isolated by two packers 530 and the drilling fluid in the isolated section 560 is pumped out (pump not shown). The packers allow at least a portion of tool 520 to be disposed in the isolated section 560 and the drilling fluid removed. The tool 520 may comprise an arm 540 that is normally closed while the tool is moving up or down in the wellbore (or during drilling for LWD tool), but can be opened when a measurement is to be made. The arm 540 may be, for example, spring-loaded and can extend to engage the borehole wall. The arm 540 may carry a measurement sub 550 comprising, for example, a laser, an optical interferometer or a stylus, a communication interface board, and a microprocessor to control the measurement parameters and perhaps to process the data. As mentioned above, the laser is used to increase the temperature of the surface and the stylus or optical interferometer is used to measure the roughness, from which TOC is calculated.

In another embodiment the arm 540 may comprise a rubber seal around the measurement sub 550. When the arm is pressed against the borehole wall, the rubber deforms and forms a hydraulic seal preventing any drilling or wellbore fluid from entering the interior region. A pump may be used to remove the small volume of drilling or wellbore fluid trapped by the rubber seal, making it possible to access the borehole wall and perform measurements. In this embodiment packers 530 and isolated section 560 are not used.

Figure 6:
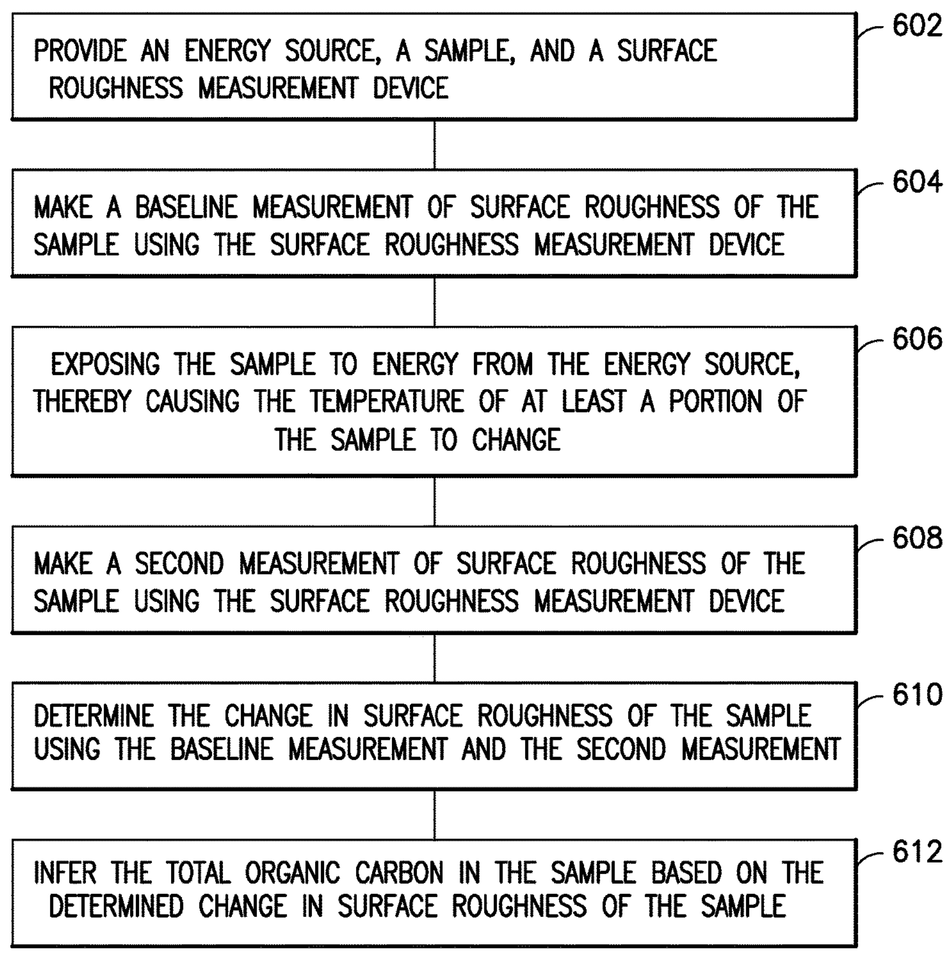
FIG. 6 is a workflow showing an embodiment of making measurements, in accordance with the present disclosure.

FIG. 6 is a flowchart of one embodiment to measure the hydrocarbon content or total organic carbon (TOC) of a rock formation. An energy source and a surface roughness measurement device are provided (602), and a baseline measurement of surface roughness of a sample is made using the surface roughness measurement device before applying energy to the sample surface (604). The sample is then exposed to energy from the energy source, thereby causing the temperature of at least a portion of the sample to change (606). A second measurement of surface roughness of the sample is made using the surface roughness measurement device (608), and the change in surface roughness of the sample is determined using the baseline measurement and the second measurement (610). The total organic carbon in the sample is inferred based on the determined change in surface roughness of the sample (612).

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions, and alterations herein without departing from the scope of the present disclosure.

The Abstract at the end of this disclosure is provided to comply with 37 C.F.R. § 1.72(b) to allow the reader to quickly ascertain the nature of the technical disclosure. It is submitted with the understanding that it will not be used to interpret or limit the scope or meaning of the claims.

While only certain embodiments have been set forth, alternatives and modifications will be apparent from the above description to those skilled in the art. These and other alternatives are considered equivalents and within the scope of this disclosure and the appended claims. Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method, comprising:

providing an energy source and a surface roughness measurement device;

making a baseline measurement of surface roughness of a sample using the surface roughness measurement device;

exposing the sample to energy from the energy source, thereby causing a temperature of at least a portion of the sample to change;

making a second measurement of surface roughness of the sample using the surface roughness measurement device;

determining a change in surface roughness of the sample using the baseline measurement and the second measurement; and inferring a total organic carbon in the sample based on the determined change in surface roughness of the sample.

2. The method of claim 1, wherein the energy source is selected from a group consisting of: a laser and an oven.

3. The method of claim 1, wherein the surface roughness measurement device is selected from a group consisting of: a stylus device, an optical device, and a scanning microscopy device.

4. The method of claim 1, wherein the sample is exposed to the energy uniformly or selectively.

5. The method of claim 1, wherein the energy source is a laser that produces radiation that is readily absorbed by one constituent component comprising the sample but not readily absorbed by any other constituent component comprising the sample.

6. The method of claim 1, wherein the sample is a shale comprising background minerals and organic patches.

7. The method of claim 6, wherein, as the sample is exposed to the energy, the organic patches thermally expand more than the background minerals.

8. The method of claim 1, wherein the sample is in situ in a wellbore, and further comprising isolating the sample from drilling fluid and/or wellbore fluid.

9. The method of claim 8, wherein the isolating the sample comprises using packers disposed in the wellbore or using a hydraulic seal to enclose the sample.

10. The method of claim 1, wherein the making a measurement comprises scanning the sample to produce a plurality of surface profiles.

11. The method of claim 10, further comprising integrating substantially equal height profile components and comparing the obtained integrated value to a corresponding total surface area of the sample.

12. An apparatus, comprising:

a tool body on which an energy source and a surface roughness measurement device are carried, the tool body being disposed in a wellbore, and wherein the energy source is capable of delivering energy to a sample, and at least the surface roughness measurement device is carried on an extendible arm of the tool body; and a sealing mechanism disposed in the wellbore and isolating a section of the wellbore, wherein at least the surface roughness measurement device and the sample are located within the isolated section of the wellbore.

13. The apparatus of claim 12, wherein the energy source is selected from a group consisting of: a laser and an oven.

14. The apparatus of claim 12, wherein the surface roughness measurement device is selected from a group consisting of: a stylus device, an optical device, and a scanning microscopy device.

15. The apparatus of claim 12, wherein the sealing mechanism is selected from the group consisting of: a pair of packers and a sealing ring.

16. The apparatus of claim 12, wherein the sealing mechanism is a pair of packers wherein one packer is sealingly engaged to a wellbore wall above the sample and the other packer is sealingly engaged to the wellbore wall below the sample.

17. The apparatus of claim 12, wherein the sealing mechanism is a sealing ring and the sealing ring is brought into sealing engagement with a wellbore wall by the extendible arm.

18. The apparatus of claim 12, wherein the energy source is a laser that produces radiation that is readily absorbed by one constituent component comprising the sample but not readily absorbed by any other constituent component comprising the sample.

19. The apparatus of claim 12, wherein the sample is a shale comprising background minerals and organic patches.

20. The apparatus of claim 19, wherein, as the sample is exposed to the energy, the organic patches thermally expand more than the background minerals.

21. A method, comprising:

providing a downhole tool that comprises an energy source and a surface roughness measurement device, and disposing the downhole tool in a wellbore that penetrates a formation;

bringing an extendible portion of the downhole tool into sealing engagement with a wall of the wellbore;

evacuating fluid within an interior region enclosed by the extendible portion of the downhole tool and the wellbore wall;

making a baseline measurement of surface roughness of a sample portion of the wellbore wall enclosing the interior region using the surface roughness measurement device;

exposing the sample portion of the wellbore wall to energy from the energy source to cause uneven thermal expansion of constituent components of the sample portion of the wellbore wall;

making a second measurement of surface roughness of the sample portion of the wellbore wall using the surface roughness measurement device;

determining a change in surface roughness of the sample portion of the wellbore wall using the baseline measurement and the second measurement; and inferring one or more formation properties based on the determined change in surface roughness of the sample portion of the wellbore wall.

22. The method of claim 21, wherein the extendible portion is selected from the group consisting of: a pair of packers and a sealing ring carried on a moveable member.

23. The method of claim 21, wherein the inferring comprises comparing a total elevated area to a corresponding total surface area.

* * * * *